(12) United States Patent
Akyuz

(10) Patent No.: US 7,390,478 B2
(45) Date of Patent: Jun. 24, 2008

(54) HAIR THICKENING COMPOSITION AND METHOD

(75) Inventor: Rafael Akyuz, Palos Verdes Estates, CA (US)

(73) Assignee: Sebastian International, Inc., Woodland Hills, CA (US)

( * ) Notice: Subject to any disclaimer, the term of this patent is extended or adjusted under 35 U.S.C. 154(b) by 790 days.

(21) Appl. No.: 10/785,765

(22) Filed: Feb. 23, 2004

(65) Prior Publication Data

US 2005/0186164 A1 Aug. 25, 2005

(51) Int. Cl.
*A61Q 5/12* (2006.01)

(52) U.S. Cl. ............... 424/70.1; 424/70.12; 424/70.15; 424/70.27; 424/70.31

(58) Field of Classification Search ........................ None
See application file for complete search history.

(56) References Cited

U.S. PATENT DOCUMENTS

| | | | |
|---|---|---|---|
| 4,041,150 A | 8/1977 | Karjala | |
| 4,076,800 A | 2/1978 | Marsh et al. | |
| 4,126,674 A | 11/1978 | Mausner | |
| 4,243,659 A | 1/1981 | Balingit et al. | |
| 4,472,375 A | 9/1984 | Bolich, Jr. et al. | |
| 4,719,099 A | 1/1988 | Grollier et al. | |
| 4,847,076 A | 7/1989 | Deshpande et al. | |
| 4,855,130 A | 8/1989 | Konrad et al. | |
| 5,047,177 A | 9/1991 | Varco | |
| 5,116,607 A | 5/1992 | Jones | |
| 5,139,770 A | 8/1992 | Shih et al. | |
| 5,181,529 A | 1/1993 | Roberts | |
| 5,288,484 A | 2/1994 | Tashjian | |
| 5,358,667 A | 10/1994 | Bergmann | |
| 5,376,364 A | 12/1994 | Darkwa et al. | |
| 5,393,305 A | 2/1995 | Cohen et al. | |
| 5,523,078 A | 6/1996 | Baylin | |
| 5,612,024 A | 3/1997 | Giede et al. | |
| 5,679,328 A | 10/1997 | Dupuis | |
| 5,711,943 A | 1/1998 | Grossman | |
| 5,964,227 A | 10/1999 | Collin | |
| 5,972,322 A | 10/1999 | Rath et al. | |
| 6,010,690 A | 1/2000 | Varco | |
| 6,010,990 A | 1/2000 | Rousso et al. | |
| 6,017,519 A | 1/2000 | Rose et al. | |
| 6,173,717 B1 * | 1/2001 | Schonert et al. ............. 132/202 |
| 6,348,439 B1 | 2/2002 | Rousso et al. | |
| 6,486,105 B1 | 11/2002 | Cannell et al. | |
| 6,521,219 B1 | 2/2003 | Hirata | |
| 2002/0176836 A9 | 11/2002 | Belli et al. | |
| 2003/0075197 A1 | 4/2003 | Kripp et al. | |
| 2003/0158065 A1 | 8/2003 | Lukenbach et al. | |

FOREIGN PATENT DOCUMENTS

| WO | WO 93/00882 | 1/1993 |
|---|---|---|
| WO | WO 99/32067 | 7/1999 |

OTHER PUBLICATIONS

"The Chemistry and Manufacture of Cosmetics. vol. II—Formulating" 2000, M. L. Schlossman, XP002327609; p. 541-p. 577; see p. 558.
"The Chemistry and Manufacture of Cosmetics" 2000, M. L. Schlossman, XP002327610; see formula 6, 7, 8, 11; p. 359-p. 392.
European Official Communication dated Aug. 16, 2006.
European Official Communication dated Mar. 28, 2007.

* cited by examiner

*Primary Examiner*—Jyothsna A Venkat
(74) *Attorney, Agent, or Firm*—Fulbright & Jaworski L.L.P.

(57) ABSTRACT

A two step method to increase the thickness of human hair in which in Step I, a high pH priming lotion is applied to pretreat the hair to increase its pH, create an anionic charge and therefore loosen and lift the cuticle layers of the hair. In Step II, an acidic thickening composition is applied on top of the Step I composition to deliver polymers and conditioning ingredients to the hair's polypeptide molecule sites. The Step II components have cationic sites that chemically bond to anionic groups in the hair, making them substantive to the hair wherein they deposit under and around the crevices of the cuticles. The low pH of Step II tightly closes the cuticles, sealing the substantive ingredients to the surface of the hair, providing the hair with increased diameter and long lasting thickness.

6 Claims, 1 Drawing Sheet

HAIR THICKENING COMPOSITION AND METHOD

FIELD OF THE INVENTION

The present invention is in the field of compositions and methods for thickening hair.

BACKGROUND OF THE INVENTION

Hair care products specifically formulated to provide body and thickness to fine hair have long been commercially available. Shampoos that are common to the marketplace are typically formulated to have pH ranges that are acidic to neutral, for example, about 5.5 to 7.0. However, as described in Rousso et al U.S. Pat. Nos. 6,010,990 and 6,348,439 ("High Alkaline Hair Compositions for Increased Fullness and Body"), many low pH to neutral pH hair shampoos do not provide lasting fullness and body to fine and very fine hair. Rousso et al contended that low pH works to close cuticles that surround the hair shaft, which decreases penetration of active ingredients and tends to decrease the diameter of the hair, resulting in a decrease in the perception of body and fullness of the hair. Rousso et al's solution was to avoid low pH formulations, to formulate the polymers in a high pH medium on the basis that the combination lifts the hair cuticle and allows the polymers to penetrate into the hair to deposit under the cuticle and attach to the hair. When the hair is rinsed, the pH returns to normal or near normal levels and the cuticles flatten, but the deposited polymer blocks the cuticle from returning to its prior flattened state, trapping the polymer to give the hair fiber more body and fullness.

Others in the art have also avoided low pH formulations. For example, Collin in U.S. Pat. No. 5,964,227 ("Method and System for Treating Damaged Hair") contended that solutions applied to the hair having a pH lower than about 4.5 tend to tighten the coiled protein structure, and under conditions of extreme acidity such solutions cause the hair to become dry, brittle and almost crystalline in structure. Hirata in U.S. Pat. No. 6,521,219 ("Method Of Repairing or Restoring Damaged or Imperfect Hair")) hydrated hair shafts to open flaps of the cuticles layer, applied amino acids or peptides to the hair shafts to nourish the hair, then sandwiched the hair shafts between heated plates to compress the hair shafts under heat, causing the amino acids or peptides to penetrate through the cuticle layer and close the openings between the flaps.

By way of further background, attention is called to the following United States Letters patent references each of which is distinguishable from the teachings of the present invention, yet representative of at least an aspect of the state of the art.

Lange U.S. Pat. No. 5,132,107 describes a two phase shampoo allowing sequential application of substances/conditions to control dandruff. The hair is washed with a neutral or alkaline pH detergent composition, which may contain an antimycotic, and after rinsing out, the scalp is treated with a composition having an acid pH in the absence of detergents, but which may also contain an antimycotic.

Shih et al U.S. Pat. No. 5,139,770 and Grossman U.S. Pat. No. 5,711,943 both describe hair thickening or swelling gels or compositions containing at least polyvinylpyrrolidone (PVP) polymers, deionized water, fragrances, PEG-10 castor oil, citric acid, aminomethyl propanol (AMP), polyquaternium-11, glycerin, and/or methylparaben as a preservative.

Varco U.S. Pat. No. 6,010,690, describes a relatively high pH (alkaline) hair conditioning composition containing cationic guar hydroxypropyltrimonium chloride (Jaguar).

Deshpande et al U.S. Pat. No. 4,847,076, describes a method for enhancing the body of hair by applying to the hair a composition containing at least Jaguar.

Dupuis U.S. Pat. No. 5,679,328, describes a hair thickening composition containing a nonionic guar gum.

Balingit et al U.S. Pat. No. 4,243,659, Grollier et al U.S. Pat. No. 4,719,099, Bolich, Jr. et al U.S. Pat. No. 4,472,375, Varco U.S. Pat. No. 5,047,177, Tashjian U.S. Pat. No. 5,288,484, Bergmann U.S. Pat. No. 5,358,667, and Darkwa et al U.S. Pat. No. 5,376,364 all describe hair thickening or conditioning shampoos, compositions, formulas, etc. which contain at least an anionic or cationic thickening or conditioning agent.

Marsh et al U.S. Pat. No. 4,076,800, Mausner U.S. Pat. No. 4,126,674, Konrad et al U.S. Pat. No. 4,855,130, Jones U.S. Pat. No. 5,116,607, and Baylin U.S. Pat. No. 5,523,078 all describe hair thickening or conditioning compositions containing such ingredients as proteins, vitamins, and others used in formulations of the present invention).

Kripp et al U.S. Patent Application Publication No. 2003/0075197, Rath et al U.S. Pat. No. 5,972,322, Roberts U.S. Pat. No. 5,181,529, Cohen et al U.S. Pat. No. 5,393,305, and Cannell et al U.S. Pat. No. 6,486,105 all describe hair conditioning and/or thickening compositions having two-step or multi-step application processes.

Lukenbach et al Belli et al U.S. Patent Application Publication No. 2003/0158065, Belli et al U.S. Patent Application Publication No. 2002/0176836, and Giede et al U.S. Pat. No. 5,612,024, show various components of hair treating formulations.

Applicant herewith incorporates by reference the teachings and disclosures of the foregoing U.S. Patent Application Publication Nos. 2002/0176836; 2003/0075197; and 2003/0158065; and the foregoing U.S. Pat. Nos. 4,076,800; 4,126,674; 4,243,659; 4,472,375; 4,719,099; 4,847,076; 4,855,130; 5,047,177; 5,116,607; 5,139,770; 5,181,529; 5,288,484; 5,358,667; 5,376,364; 5,393,305; 5,523,078; 5,612,024; 5,679,328; 5,711,943; 5,964,227; 5,972,322; 6,010,690; 6,010,990; 6,348,439; 6,486,105; and 6,521,219.

SUMMARY OF THE INVENTION

The present invention departs radically from the foregoing art by incorporating its effective components, e.g., thickener, conditioner and humectant components, in an acidic formulation, and in doing so dramatically and surprisingly improves the thickness of hair unlike any other hair thickening product. This is accomplished by a two step method to increase the thickness of human hair in which in Step I, a high pH priming lotion is applied to pre-treat the hair to increase its pH, create an anionic charge and therefore loosen and lift the cuticle layers of the hair. In Step II, an acidic thickening composition is applied on top of the Step I composition to deliver polymers and conditioning ingredients to the hair's polypeptide molecule sites. The Step II components have cationic sites that chemically bond to anionic groups in the hair, making them substantive to the hair wherein they deposit under and around the crevices of the cuticles. The low pH of Step II tightly closes the cuticles, sealing the substantive ingredients to the surface of the hair, providing the hair with increased diameter and long lasting thickness that is semi-permanent and more pronounced than that of common hair thickening compositions.

More particularly, the present invention is directed to treating hair to increase its thickness in which hair is pre-treated by applying a high pH composition to the hair, which serves to lift cuticle layers of the hair. A low pH composition is then applied which contains a thickening agent that becomes substantive to the hair, the low pH substantially neutralizing the high pH composition causing the cuticles to close and seal the thickening agent to the hair.

In particular embodiments, the high pH composition is formed from water, a basic pH adjuster, a rheology control agent, a conditioning agent, and a solubilizer for the conditioning agent, and further can include one or more preservatives and a fragrance. Again in particular embodiments, the low pH composition is formed from water, a thickening agent, an acidic pH adjuster, a humectant, one or more conditioning agents, one or more film forming hair fixatives, an emollient, and a solubilizer for the emollient, and can also include one or more preservatives and a fragrance.

The method and formulations of the present invention can be used not only by professional stylists in hair salons, but the ease of simply applying successive formulations makes it convenient to be packaged as a kit for use at home or at a salon. Thus the invention includes a method for treating hair, the high and low pH compositions as such, and a kit comprised of the high and low pH compositions. Still further advantages and benefits will be apparent to those skilled in the art from the drawings, description, examples and claims which follow.

DETAILED DESCRIPTION OF THE INVENTION

Figure 1:
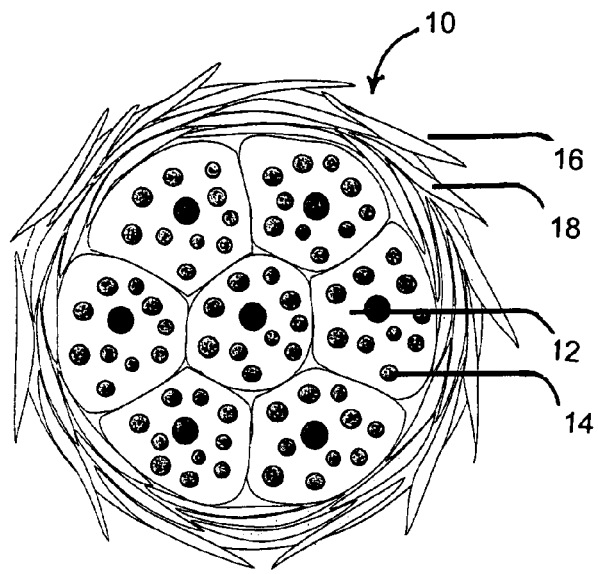
FIG. 1 schematically depicts the cross section of a strand of hair after application of Step I of the invention; and FIG. II schematically depicts the cross section of the strand of hair of FIG. 1 after application of Step II of the invention.
Figure 2:
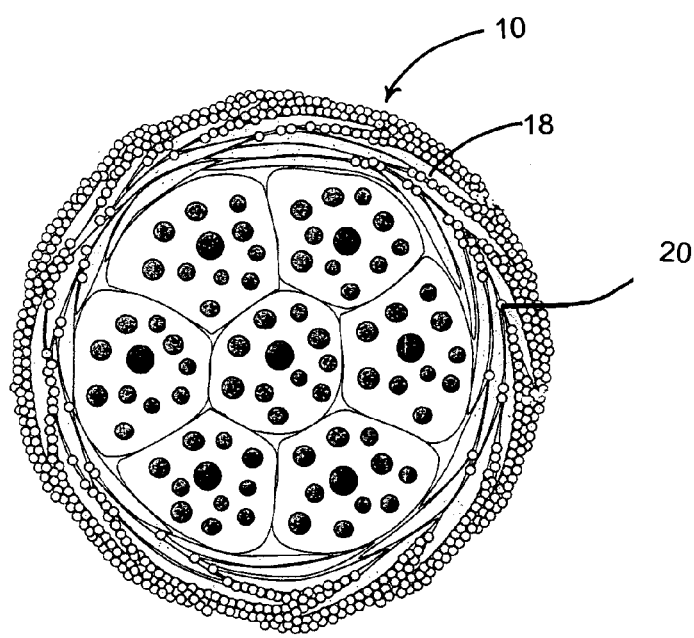

The invention provides a two step method to increase the thickness of human hair. Referring to FIG. 1, a cross-section of a strand of hair is shown after application of Step I in which a high pH priming lotion is applied to the hair. The hair strand 10 comprises cortical cells 12 that contain macrofibrils 14 and are surrounded by a layer 16 of cuticle cells 18 that are loosened and lifted by an anionic charge created by application of the high pH composition. FIG. 2 shows a cross-section of the strand 10 after Step II in which an acidic thickening composition is applied on top of the Step I composition to deliver polymers and conditioning ingredients to the hair's polypeptide molecule sites, shown at 20. The Step II components have cationic sites that chemically bond to anionic groups in the hair, making them substantive to the hair wherein they deposit under and around the crevices of the cuticles 18. The low pH of Step II tightly closes the cuticles 18, sealing the substantive ingredients to the surface of the hair, providing the hair with increased diameter and long lasting thickness that is semi-permanent and more pronounced than that of common hair thickening compositions.

Thus in Step 1 of the method of the invention, the hair is pre-treated by applying a high pH composition to the hair whereby to lift cuticle layers of the hair. Thereafter, in Step II, a low pH composition containing a thickening agent, and adjuvants, is applied to the pre-treated hair to make the thickening agent substantive to the hair and to close the cuticles to seal the thickening agent to the hair. A sufficient amount of the low pH composition is applied to the high pH composition to substantially neutralize the high pH composition. It is preferred to formulate the high and low pH compositions so that an amount of low pH composition equal to the amount applied of the high pH priming composition neutralizes the high pH composition. However, other ratios will be useful and exactitude is not necessary. Following application of the neutralizing low pH composition, retention of the thickener is sufficiently strong that the hair can be thoroughly washed without loss of the thickening benefits provided by the invention.

General Compositions and Methods

Preferably, the high pH composition has a pH of at least 9.00, most preferably in the range of 9.00-9.50 (pH @ 25° C.), and has a viscosity of 500 to 20,000 cps (RVT: #2 @ 10 rpmc @ 25° C.). In a particular embodiment, the high pH composition is formed from water, a basic pH adjuster, a rheology control agent, a conditioning agent, and a solubilizer for the conditioning agent. For example, the high pH composition can have the following composition, based on the weight of the high pH composition:

0.50-5.00% conditioning agent;
0.50-5.00% solubilizer for the conditioning agent;
0.01-1.00% rheology control agent; and
water and sufficient basic pH adjuster to bring the pH of the composition to a range of 9.00-9.50.

The high pH composition can further comprise one or more preservatives and a fragrance. For example, from 0.05 to 1.00% by weight of one or more preservatives can be added, exemplified by 1.00% by weight. Again by example, 0.01 to 1.00% by weight of a fragrance can be added, exemplified by 0.10% by weight.

The high pH composition can be prepared by dispersing the rheology control agent in water with mixing until clear and lump free to form a first Step I formulation. The pH of the first Step I formulation is then adjusted to 9.00-9.50 with the basic pH adjuster. Separately, a conditioning agent and a solubilizer for the conditioning agent are mixed to form a second Step I formulation, which is added to and mixed with the first Step I formulation until uniform. One or more preservatives and fragrance can be added to the second Step I formulation.

Preferably, the low pH composition has a pH equal to or lower than 4.50, most preferably in the range of 3.80-4.50 (pH @ 25° C.), and also has a viscosity of 500 to 20,000 cps. (RVT: #2 @ 10 rpmc @ 25° C.). In a particular embodiment, the low pH composition is formed from water, an acidic pH adjuster, a humectant, one or more conditioning agents (which are preferably cationic conditioning agents so as to better adhere to the anionic groups present in the hair), one or more film forming hair fixatives, an emollient, and a solubilizer for the emollient. For example, the low pH composition can have the following composition, based on the weight of the low pH composition:

0.01-2.00% of the thickening agent;
1.21-25.00% one or more conditioning agents;
1.00-17.00% one or more film forming hair fixatives;
0.10-4.00% humectant;
0.05-1.00% emollient;
0.50-2.00% solubilizer for the emollient; and
water and sufficient acidic pH adjuster to bring the pH of the composition to a range of 3.80-4.50.

Here, too, the low pH composition can further comprise one or more preservatives and a fragrance. For example, from 0.05 to 1.00% by weight of one or more preservatives can be added, exemplified by 1.00% by weight. Again by example, 0.01 to 1.00% by weight of a fragrance can be added, exemplified by 0.10% by weight.

The low pH composition can be prepared by dispersing the thickening agent in water with mixing to form a first Step II formulation, which is heated to a temperature of about 65 to 85° C., exemplified by 70° C. Humectant is slurried with a conditioning agent to form a second Step II formulation, which is added to the first formulation at the above temperature and mixed until uniform to form a third Step II formulation. The third Step II formulation is cooled to a temperature of about 30 to 40° C., exemplified by 40° C. and its pH adjusted to 3.80-4.50 with an acidic pH adjuster. Other conditioning agents and the film forming hair fixatives are added to the third Step II formulation to form a fourth Step II formulation. The emollient and the solubilizer for the emollient are mixed to form a fifth Step II formulation, which is added to, and mixed with, the fourth Step II formulation until uniform. One or more preservatives and fragrance can be added to the fifth Step II formulation.

The following will describe many of the foregoing ingredients in more detail. These and other cosmetic additives commonly used in personal care formulations are described in, for example, International Cosmetic Ingredient Dictionary and Handbook (7.sup.th Ed.) vol. 1-3 (1997), The Cosmetic, Toiletry and Fragrance Association, Washington, D.C.

Rheology Control Agent

Nonionic polymers can be used as rheology control agents. Such polymers suitable for use in the invention are generally classified as water soluble nonionic poly(ethylene oxide) homopolymers (e.g., polyethylene glycols). Non-limiting examples of particular grades of polyethylene glycol (Polyox) water soluble resins suitable for use in the present invention include: Polyox WSR-301 (CTFA name PEG-90M, MW: 4,000,000) sold by Union Carbide; Polyox coagulant (CTFA name PEG-115M, MW: 5,000,000); and Polyox WSR N-60K (CTFA name PEG-45M, MW: 2,000,000).

Thickening Agent

As used herein, the term "thickening agent" means any agent whose function is to increase the viscosity of the composition. The nonionic amphiphilic polymers are preferred, which comprise at least one fatty chain and at least one hydrophilic unit, and may, for example, be chosen from: (1) celluloses modified with groups comprising at least one fatty chain, for example hydroxyethylcelluloses, such as sold by the company Amerchol under the trade name Cellossize Polymer PCG-10, as well as celluloses modified with groups comprising at least one fatty chain chosen from alkyl, arylalkyl and alkylaryl groups, and in which the alkyl groups are, for example, $C_8$-$C_{22}$, such as the product Natrosol Plus Grade 330 CS($C_{16}$ alkyls) sold by the company Aqualon, and the product Bermocoll EHM 100 sold by the company Berol Nobel, and celluloses modified with polyalkylene glycol alkylphenyl ether groups, such as the product Amercell Polymer HM-1500 (polyethylene glycol (15) nonylphenyl ether) sold by the company Amerchol; (2) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie; (3) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas; (4) copolymers of vinylpyrrolidone and of fatty-chain hydrophobic monomers; examples that may be mentioned include the products Antaron V216 and Ganex V216 (vinylpyrrolidone/hexadecene copolymer) sold by the company I.S.P., the products Antaron V220 and Ganex V220 (vinylpyrrolidone/eicosene copolymer) sold by the company I.S.P.; (5) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208; and (6) copolymers of hydrophilic acrylates or methacrylates and of hydrophobic monomers comprising at least one fatty chain, such as polyethylene glycol methacrylate/lauryl methacrylate copolymer. A non-ionic surfactant such as PEG-150 Distearate, Oleth-20, Steareth-21, Ceteth-20, Laureth-23, Nonoxynol-4, Nonoxynol-20, Lauramide DEA, Cocamide MEA, Polysorbate-20, lauryl polyglucoside, sucrose laurate, and polyglycerol 8-oleate.

See also, the thickeners described in U.S. Patent Application Publication 2003/0147827, the content thereof being entirely incorporated by reference.

It will be appreciated that some materials referred to as thickening agents, can alternatively serve as conditioning agents in the formulations, so there will be some duplication of materials under the conditioning agent category.

Humectant

Specific examples of humectants include: glycerin, butylene glycol, sorbitol, propylene glycol, glycereth-7, glycereth-12, glycereth-26, glycereth-31, methyl gluceth-10, methyl gluceth-20, PEG4, polyamino sugar condensate, polyquaternium-7, polyquaternium-22, polyquaternium-39, polyquaternium-47, PCA, sodium PCA, and UREA, and mixtures thereof.

Step I Conditioning Agent

Conditioners that can be used in Step I are silicones, such as volatile and non-volatile silicones, as for example polyalkylsiloxanes (optionally end-capped with one or more hydroxyl groups), polyalkylaryl siloxanes, siloxane gums and resins, cyclomethicones, aminofunctional silicones, quaternary silicones and mixtures thereof. Preferred silicones include polydimethylsiloxanes (CTFA name dimethicone) (which in the present invention are advantageously coupled with a polyethylene glycol such as PEG-12, sold under the trade name Dow Corning 193), siloxane gums, aminofunctional silicones (CTFA name amodimethicone) and hydroxylated polydimethylsiloxanes (CTFA name dimethiconol).

Solubilizer for Step I Conditioning Agent

A nonionic surfactant can be used as a solubilizer for the Step I conditioning agent. A preferred nonionic surfactant is polysorbate 20, a laurate monoester of a mixture of sorbitol and sorbitol anhydrides condensed with approximately 20 moles of ethylene oxide), sold by Uniqema as Tween 20. Other suitable nonionic surfactants that can be used as solubilizers include long chain alkyl glucosides having alkyl groups containing about 8 carbon atoms to about 22 carbon atoms, coconut fatty acid monoethanolamides such as cocamide MEA, coconut fatty acid diethanolamides, and polyoxyethylene derivatives of polyol esters. Specific examples include: decyl polyglucoside (available as APG 325 CS from Cognis) and lauryl polyglucoside (available as APG 600CS and 625 CS from Cognis); sucrose cocoate, sucrose laurate, dimethyl-dodecylamine oxide, oleyldi(2-hydroxyethyl)amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylam-ine oxide, 2-dodecoxyethyldimethylamine oxide, 3-dodecoxy-2-hydroxypropyld-i(3-hydroxypropyl)amine oxide, dimethylhexadecylamine oxide, lauramine oxide, and cocoamine oxide; and Atlas G-4280 (PEG-80 sorbitan laurate, a sorbitan monoester of lauric acid ethoxylated with an average of about 80 moles of ethylene oxide).

Step II Conditioning Agent

The invention uses cationic conditioning agents such as: a cationic cellulose derivative; a cationic guar derivative; a homopolymer or copolymer of a cationic monomer; cationic cellulose derivatives, such as the polymeric quaternary ammonium salt derived from the reaction of hydroxyethyl cellulose with a trimethylammonium substituted epoxide. The material known as Polyquaternium-11, commercially available from ISP as Gafquat 755NP-W is particularly useful. The cationic guar derivative is preferably a guar hydroxypropyltrimonium chloride, such as hydroxypropyl guar hydroxypropyltrimonium chloride, available commercially from Rhodia under the trade name, "Jaguar C-162." Other suitable cationic polymer includes those compounds derived from acrylamidopropyl trimonium chloride and copolymer thereof with acrylamide, the latter of which is available commercially from Allied Colloids, of Suffolk, Va. under the trade name, "Salcare SC60." Still other suitable cationic conditioning polymers are those derived from the monomer diallyldimethylammonium chloride. The homopolymer of this monomer is Polyquaternium-6, which is available commercially from Allied Colloids of Suffolk, Va. under the trade name, "Salcare SC30." The copolymer of diallyldimethylammonium chloride with acrylamide is known as Polyquaternium-7, and is also available from Allied Colloids under the trade name "Salcare SC10." Other suitable polymers include polyquaternium-47, which is available from Calgon Corporation under the trade name, "MERQUAT 2001N."

See also, the cationic conditioners described in U.S. Patent Application Publication 2003/0176303, the content thereof being entirely incorporated by reference.

Another class of useful conditioners include amino acids derived from the hydrolysis of various proteins as well as the salts, esters, and acyl derivatives thereof. Examples of such amino acids include: wheat amino acids; amphoteric/zwitterionic amino acids such as alkylamido alkylamines; stearyl acetyl glutamate; capryloyl silk amino acids; capryloyl collagen amino acids; capryloyl keratin amino acids; capryloyl pea amino acids; cocodimonium hydroxypropyl silk amino acids; corn gluten amino acids; cysteine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; and other silk amino acids; and mixtures thereof.

Still other useful conditioning agents such as: panthenol, such as D-Panthenol available from Roche, hydrolysed collagen with trade name Peptein 2000 available from Hormel, hydrolysed keratin, proteins, and herbal extracts such as polygonatum multiflori extract.

Film Former/Hair Fixative

Polymers with film-forming properties can be used as hair fixative resins. Preferably, the film-forming polymers are polyvinylpyrrolidone (PVP) in type, or copolymers of polyvinylpyrrolidone and methyl methacrylate, polyvinylpyrrolidone and vinyl acetate (VA) copolymers, ethylene glycol polyterephthalate/polyethylene glycol copolymers, ethylene glycol polyterephthalate/polyethylene glycol/sodium polyisophthalate sulphonate copolymers, and mixtures thereof.

Basic pH Adjuster

Suitable basic pH adjusters include (1) ammonia and organic amines, such as aminomethyl propanol, triethyl amine, triethanol amine, methyl amine, and morpholine, and (2) metal hydroxides such as sodium and potassium hydroxide, oxides, and carbonates, etc.

Acidic pH Adjuster

Suitable acidic pH adjusters include citric acid, carboxylic acids such as acetic acid, and mineral acids, such as HCl.

Emollient

Emollients are typically water-immiscible, oily or waxy materials which condition the hair and scalp and assist in the ease of combing, detangling, body, shine, manageability, split-end mending and preventing static build-up. A wide variety of suitable emollients are known and may be used herein. Preferred emollients are straight and branched chain hydrocarbons having from about 7 to about 40 carbon atoms, such as isohexadecane sold under the trade name Permethyl 101A by Presperse Inc., South Plainfield, N.J. Other suitable emollients include dodecane, squalane, cholesterol, hydrogenated polyisobutylene, isoeicosane, isooctahexacontane, isohexapentacontahectane, and the $C_7$-$C_{40}$ isoparaffins, which are $C_7$-$C_{40}$ branched hydrocarbons.

See also, the emollients described in U.S. Patent Application Publication 2002/0155962, the content thereof being entirely incorporated by reference.

Solubilizer for Emollient

A nonionic surfactant, such as those described with respect to the Step I conditioning agent solubilizer, can also be used as a solubilizer for the emollient, but it is preferred to use surfactants with greater affinity for the hydrocarbon compounds used as emollients herein. Such solubilizers are exemplified by ethoxylated surfactants having between 1 and 1000 ethylene oxide units, such as the fatty acid ester ethoxylates, fatty alcohol ethoxylates, fatty amine ethoxylates, and fatty acid alkanol amide ethoxylates, Specific examples include: hydrogenated castor oil with the INCI name PEG-40 hydrogenated castor oil, sold by BASF under the trademark Cremophor RH-40; castor oil ethoxylated with 25 ethylene oxide units designated by the INCI name, PEG-25 hydrogenated castor oil, also sold by BASF; and diglyceride ethoxylates, sold by ICI under the trademark Arlatone RTM G Preservative Preservatives for compositions of this invention can include alkyl esters of para-hydroxybenzoic acid, hydantoin derivatives, propionate salts, and a variety of other known preservatives. Specific examples include: phenoxyethanol, methyl paraben, ethylparaben, butylparaben, isobutylparaben, propyl paraben, isomethyl paraben, isopropyl paraben, benzyl alcohol, imidazolidinyl urea, triclosan (5-chloro-2-(2, 4-dichlorophenoxy) phenol), 1,3-bis (hydroxymethyl)-5,5-dimthylhydantoin, benzalkonium chloride, benzethonium chloride, methylbenzethonium chloride, sodium benzoate, iodopropynyl butylcarbamate, and mixtures thereof.

Fragrance

A wide variety of fragrances are available to suit any olfactory taste. Two used in examples of the present invention are "Wild Pamplemouse" #VV76-00475, sold by Ungerer, and #UL031649, sold by Givaudan.

The following examples, in which all parts are by weight %, will further illustrate the invention.

EXAMPLE 1

Step I High pH Composition

A high pH composition can be prepared in which in which: the conditioning agent is PEG-12 dimethicone; the solubilizer for the conditioning agent is polysorbate 20; the rheology control agent is PEG-90M; the pH adjuster is aminomethyl propanol; and the preservatives are a combination of phenoxyethanol, methylparaben, ethylparaben, butylparaben, isobutylparaben, and propylparaben. The following sets forth ranges for each of these ingredients. The amounts are by weight based on the weight of the high pH composition:

87.40-97.84% deionized water;
0.01-1.00% PEG-90M;
0.05-0.50% aminomethyl propanol;
0.50-5.00% polysorbate 20;
0.50-5.00% PEG-12 dimethicone;

0.05-1.00% combination of phenoxyethanol, methyl paraben, ethylparaben, butylparaben, isobutylparaben, propyl paraben preservatives; and 0.01-1.00% fragrance (Wild Pamplemouse #W76-00475).

The PEG-90M is dispersed in water with mixing until clear and lump free to form a first Step I formulation. The pH of the first Step I formulation is then adjusted to 9.00-9.50 with the aminomethyl propanol. Separately, the PEG-12 dimethicone and polysorbate 20 are mixed to form a second Step I formulation, which is added to and mixed with the first Step I formulation until uniform. The preservatives and fragrance are added to the second Step I formulation.

EXAMPLE 2

Specific Step I High pH Composition

A high pH composition was prepared following the procedure of Example 1. The amounts are by weight based on the weight of the high pH composition.

95.40% deionized water;
0.20% PEG-90M;
0.30% aminomethyl propanol;
1.50% polysorbate 20;
1.50% PEG-12 dimethicone;
1.00% combination of phenoxyethanol, methyl paraben, ethylparaben, butylparaben, isobutylparaben, propyl paraben preservatives; and
0.10% fragrance (Wild Pamplemouse #VV76-00475).

EXAMPLE 3

Step II Low pH Composition

A low pH composition can be prepared in which in which: in which: the thickening agent is hydroxyethyl cellulose; the conditioning agents are a combination of hydroxypropyl guar hydroxypropyltrimonium chloride, panthenol, wheat amino acids, PEG-12 dimethicone, and polyquaternium-11; the film forming hair fixatives are a combination of olyvinylpyrolidone and polyquaternium-44; the humectant is glycerin; the emollient is isohexadecane; the solubilizer for the emollient is PEG-40 hydrogenated castor oil; the acidic pH adjuster is citric acid; and the preservatives are a combination of phenoxyethanol, methylparaben, ethylparaben, butylparaben, isobutylparaben, and propylparaben. The amounts are by weight based on the weight of the high pH composition.

47.00-95.62% deionized water;
0.01-2.00% hydroxyethylcellulose;
0.10-4.00% glycerin;
0.01-2.00% hydroxypropyl guar hydroxypropyltrimonium chloride;
0.01-0.50% citric acid;
0.50-5.00% panthenol;
0.10-5.00% wheat amino acids;
0.10-3.00% PEG-12 dimethicone;
0.50-8.00% polyvinylpyrolidone;
0.50-9.00% polyquaternium-44;
0.50-10.00% polyquaternium-11;
0.50-2.00% PEG-40 hydrogenated castor oil;
0.05-1.00% combination of phenoxyethanol, methyl paraben, ethylparaben, butylparaben, isobutylparaben, propyl paraben preservatives;
0.05-1.00 isohexadecane; and
0.01-1.00% fragrance (#UL031649).

The hydroxyethylcellulose is dispersed in water with mixing to form a first Step II formulation, which is heated to a temperature of 70° C. The glycerin is slurried with the hydroxypropyl guar hydroxypropyltrimonium chloride to form a second Step II formulation, which is added to the first formulation at 70° C. and mixed until uniform to form a third Step II formulation. The third Step II formulation is cooled to a temperature of 40° C. and its pH adjusted to 3.80-4.50 with the citric acid. The panthenol, wheat amino acids, PEG-12 dimethicone, polyvinylpyrolidone, polyquaternium-44, and polyquaternium-11 are added to the third Step II formulation to form a fourth Step II formulation. The isohexadecane and the PEG-40 hydrogenated castor oil are mixed to form a fifth Step II formulation, which is added to, and mixed with, the fourth Step II formulation until uniform. The preservatives and fragrance are added to the fifth Step II formulation.

EXAMPLE 4

Specific Step II Low pH Composition

A low pH composition was prepared following the procedure of Example 3. The amounts are by weight based on the weight of the low pH composition.

68.40% deionized water;
0.50% hydroxyethylcellulose;
2.00% glycerin;
0.50% hydroxypropyl guar hydroxypropyltrimonium chloride;
0.10% citric acid;
4.00% panthenol;
1.00% wheat amino acids;
1.50% PEG-12 dimethicone;
6.00% polyvinylpyrolidone;
5.00% polyquaternium-44;
7.00% polyquaternium-11;
2.00% PEG-40 hydrogenated castor oil;
1.00% combination of phenoxyethanol, methyl paraben, ethylparaben, butylparaben, isobutylparaben, propyl paraben preservatives;
0.50% isohexadecane; and
0.50% fragrance (#UL031649).

EXAMPLE 5

Method of Applying

The hair of a person to be treated by applying the two step procedure of this invention is pre-treated by applying the high pH composition of Example 2 to the hair whereby to lift cuticle layers of the hair. Thereafter, the low pH composition of example 4 is applied to the pre-treated hair to make the hydroxyethylcellulose thickening agent substantive to the hair and to close the cuticles to seal the thickening agent to the hair. The hair is then washed without loss of the thickening benefits provided by the invention.

EXAMPLE 6

Providing as a Kit

A kit for treating hair to increase its thickness is formed by packaging together with instructions for use, a bottle of the high pH composition of Example 2 for pre-treating the hair to lift cuticle layers of the hair, and a bottle of the low pH composition of Example 4 for application to the pre-treated hair to enable the thickening agent to be substantive to the hair and close the cuticles to seal the thickening agent to the hair.

The invention claimed is:

1. A method of treating hair to increase its thickness, comprising:
   pre-treating the hair by applying a high pH composition to the hair whereby to lift cuticle layers of the hair; and
   thereafter, applying a low pH composition containing a thickening agent to said pre-treated hair whereby to make the thickening agent substantive to the hair and closing the cuticles to seal the thickening agent to the hair;
   wherein the high pH composition comprises, based on the weight of the high pH composition:
   0.50-5.00% conditioning agent;
   0.50-5.00% solubilizer for the conditioning agent;
   0.01-1.00% rheology control agent;
   one or more preservatives;
   a fragrance; and
   water and sufficient basic pH adjuster to bring the pH of the composition to a range of 9.00-9.50; and
   wherein the conditioning agent is PEG-12 dimethicone; the solubilizer for the conditioning agent is polysorbate 20; the rheology control agent is PEG-90M; the pH adjuster is aminomethyl propanol; and the preservatives are a combination of phenoxyethanol, methylparaben, ethylparaben, butylparaben, isobutylparaben, and propylparaben.

2. A method of treating hair to increase its thickness, comprising:
   pre-treating the hair by applying a high pH composition to the hair whereby to lift cuticle layers of the hair; and
   thereafter, applying a low pH composition containing a thickening agent to said pre-treated hair whereby to make the thickening agent substantive to the hair and closing the cuticles to seal the thickening agent to the hair;
   wherein the high pH composition is formed from, based on the weight of the high pH composition:
   87.40-97.84% deionized water;
   0.01-1.00% PEG-90M;
   0.05-0.50% aminomethyl propanol;
   0.50-5.00% polysorbate 20; and
   0.50-5.00% PEG-12 dimethicone.

3. A method of treating hair to increase its thickness, comprising:
   pre-treating the hair by applying a high pH composition to the hair whereby to lift cuticle layers of the hair; and
   thereafter, applying a low pH composition containing a thickening agent to said pre-treated hair whereby to make the thickening agent substantive to the hair and closing the cuticles to seal the thickening agent to the hair;
   wherein the low pH composition comprises, based on the weight of the low pH composition:
   0.01-2.00% of the thickening agent;
   1.21-25.00% one or more conditioning agents;
   1.00-17.00% one or more film forming hair fixatives;
   0.10-4.00% humectant;
   0.05-1.00% emollient;
   0.50-2.00% solubilizer for the emollient;
   one or more preservatives;
   a fragrance; and
   water and sufficient acidic pH adjuster to bring the pH of the composition to a range of 3.80-4.50; and
   wherein the thickening agent is hydroxyethyl cellulose; the conditioning agents are a combination of hydroxypropyl guar hydroxypropyltrimonium chloride, panthenol, wheat amino acids, PEG-12 dimethicone, and polyquaternium-11; the film forming hair fixatives are a combination of polyvinylpyrolidone and polyquaternium-44; the humectant is glycerin; the emollient is isohexadecane; the solubilizer for the emollient is PEG-40 hydrogenated castor oil; the acidic pH adjuster is citric acid; and the preservatives are a combination of phenoxyethanol, methylparaben, ethylparaben, butylparaben, isobutylparaben, and propylparaben.

4. A method of treating hair to increase its thickness, comprising:
   pre-treating the hair by applying a high PH composition to the hair whereby to lift cuticle layers of the hair; and
   thereafter, applying a low pH composition containing a thickening agent to said pre-treated hair whereby to make the thickening agent substantive to the hair and closing the cuticles to seal the thickening agent to the hair;
   wherein the low pH composition is formed from, based on the weight of the low pH composition:
   47.00-95.62% deionized water;
   0.01-2.00% hydroxyethylcellulose;
   0.10-4.00% glycerin;
   0.01-2.00% hydroxypropyl guar hydroxypropyltrimonium chloride;
   0.01-0.50% citric acid;
   0.50-5.00% panthenol;
   0.10-5.00% wheat amino acids;
   0.10-3.00% PEG-12 dimethicone;
   0.50-8.00% polyvinylpyrolidone;
   0.50-9.00% polyquaternium-44;
   0.50-10.00% polyquaternium-11;
   0.50-2.00% PEG-40 hydrogenated castor oil; and
   0.05-1.00% isohexadecane.

5. A kit for treating hair to increase its thickness, comprising:
   a high pH composition for pre-treating the hair to lift cuticle layers of the hair; and
   a low pH composition containing a thickening agent for applying to said pre-treated hair to enable the thickening agent to be substantive to the hair and close the cuticles to seal the thickening agent to the hair;
   wherein the high pH composition is formed from, based on the weight of the high pH composition:
   87.40-97.84% deionized water;
   0.01-1.00% PEG-90M;
   0.05-0.50% aminomethyl propanol;
   0.50-5.00% polysorbate 20; and
   0.50-5.00% PEG-12 dimethicone;
   wherein sufficient aminomethyl propanol is added to bring the pH of the composition to a range of 9.0-9.5.

6. A kit for treating hair to increase its thickness, comprising:
   a high pH composition for pre-treating the hair to lift cuticle layers of the hair; and
   a low pH composition containing a thickening agent for applying to said pre-treated hair to enable the thickening agent to be substantive to the hair and close the cuticles to seal the thickening agent to the hair;
   wherein the low pH composition is formed from, based on the weight of the low pH composition:
   47.00-95.62% deionized water;
   0.01-2.00% hydroxyethylcellulose;
   0.10-4.00% glycerin;
   0.01-2.00% hydroxypropyl guar hydroxypropyltrimonium chloride;
   0.01-0.50% citric acid;
   0.50-5.00% panthenol;

0.10-5.00% wheat amino acids;
0.10-3.00% PEG-12 dimethicone;
0.50-8.00% polyvinylpyrolidone;
0.50-9.00% polyquaternium-44;
0.50-10.00% polyquaternium-11;
0.50-2.00% PEG-40 hydrogenated castor oil; and
0.05-1.00% isohexadecane;
wherein sufficient citric acid is added to bring the pH of the composition to a range of 3.80-4.50.

* * * * *